(12) United States Patent
Bhaskaran et al.

(10) Patent No.: US 8,563,601 B2
(45) Date of Patent: Oct. 22, 2013

(54) METHOD OF MANAGING BRONCHO-CONSTRICTIVE CONDITION

(75) Inventors: Sunil Bhaskaran, Maharashtra (IN); Mohan Vishwaraman, Maharashtra (IN)

(73) Assignee: Indus Biotech Private Limited, Pune (IN)

( * ) Notice: Subject to any disclaimer, the term of this patent is extended or adjusted under 35 U.S.C. 154(b) by 26 days.

(21) Appl. No.: 13/192,306

(22) Filed: Jul. 27, 2011

(65) Prior Publication Data
US 2012/0190736 A1 Jul. 26, 2012

(30) Foreign Application Priority Data
Jul. 28, 2010 (IN) .......................... 2145/MUM/2010

(51) Int. Cl.
*A61K 31/353* (2006.01)
*A61P 11/06* (2006.01)
*A61P 11/00* (2006.01)

(52) U.S. Cl.
USPC ........................................ 514/456

(58) Field of Classification Search
USPC ........................................ 514/456
See application file for complete search history.

(56) References Cited

U.S. PATENT DOCUMENTS

| 2008/0044453 A1* | 2/2008 | Kobayashi et al. ........... 424/439 |
| 2010/0111927 A1* | 5/2010 | Kim ............................ 424/130.1 |
| 2011/0039923 A1 | 2/2011 | Bhaskaran et al. |

FOREIGN PATENT DOCUMENTS

| JP | 2006096693 A * | 4/2006 |
| WO | WO2007053641 | 5/2007 |

* cited by examiner

*Primary Examiner* — Yong Chong
*Assistant Examiner* — Jason A Deck
(74) *Attorney, Agent, or Firm* — DLA Piper LLP (US)

(57) ABSTRACT

The present disclosure is in relation to the use of a composition comprising pentameric type A procyanidin, trimeric procyanidin and tetrameric procyanidin, optionally along with pharmaceutical excipient(s), in management of broncho-constrictive conditions such as Allergic Rhinitis, Asthma, and Chronic obstructive pulmonary disease (COPD).

11 Claims, No Drawings

METHOD OF MANAGING BRONCHO-CONSTRICTIVE CONDITION

TECHNICAL FIELD

The present disclosure is related to management of broncho-constrictive conditions like Allergic Rhinitis, Asthma, and Chronic obstructive pulmonary disease (COPD). The broncho-constrictive condition is managed by administering a composition comprising pentameric type A procyanidin, trimeric procyanidin and tetrameric procyanidin, optionally along with pharmaceutical excipient(s).

BACKGROUND AND PRIOR ART

Catechins are polyphenolic plant metabolites which belong to the flavonoid family. The molecular formula and weight of catechins are $C_{15}H_{14}O_6$ and 290 g/mol. Catechin and epicatechin are epimers, with (−)-epicatechin and (+)-catechin being the most common optical isomers found in nature. Procyanidins or condensed tannins are flavonoid oligomers whose building blocks are (+)-catechin and (−)-epicatechin. They are present abundantly in the plant kingdom in fruits, barks, leaves and seeds where they provide protection against light, oxidation and predators. Procyanidins are found in many plants, mainly apples, pine bark, cinnamon bark, litchi pericarp, peanuts, grape seed, cocoa, grape skin, bilberry, cranberry, black currant, green tea and black tea.

Based on the linkage between the successive monomeric units, procyanidins are classified as Types A, B or C polyphenols. Generally the linkage between successive monomeric units of procyanidins is between the $4^{th}$ position of the 'upper' unit and the $8^{th}$ position of the 'lower' unit, leading to a Type B procyanidin. Alternatively, the linkage can occur between $C_4$ of the 'upper' unit and $C_6$ of the lower unit, leading to a Type C procyanidin. Type B and C polyphenols are abundantly seen in many botanical sources. When successive monomeric units are linked by an ether linkage between the C2 and C4 of the 'upper' unit and the oxygen at the C7 position and the $C^6/C^8$ positions (respectively) of the lower unit, a Type A procyanidin is formed.

Broncho-constrictive conditions are characterized by symptoms of significantly reduced ability to breathe along with coughing and wheezing. This condition produces adverse impact on the airways or bronchioles, which carry air between the bronchi and the alveoli. Inflammation of the bronchioles and clamping of the smooth muscle outside of the bronchioles cause reduced passage of air in or out of the lungs.

Allergic Rhinitis is the most common chronic respiratory illness. It affects quality of life, productivity and is associated with co-morbid conditions such as Asthma. Symptoms of Allergic Rhinitis include rhinorrhea, nasal congestion, obstruction, and pruritus which are triggered by contact with allergens like bacteria, viruses, animal parasites, dust, pollen, chemicals, food, drugs, smoke etc. Asthma is a similar chronic broncho-constrictive condition with airway restriction, mucus production and allergic reaction.

Chronic obstructive pulmonary disease (COPD) is yet another lung disease characterized by chronic bronchitis with symptoms of cough with mucus, wheezing, shortness of breath, fatigue, frequent respiratory infections etc. There is no cure for COPD. Some of the medications used for treatment of COPD are bronchodilators to open the airways, such as ipratropium, tiotropium, salmeterol, or formoterol; and inhaled steroids to reduce lung inflammation.

Bhaskaran et al. (US 2011/0039923 A1) discloses a composition comprising pentameric procyanidin flavonoid of concentration ranging from about 55% w/w to about 99% w/w, trimers and tetramers each at a concentration ranging from about 0.5% w/w to about 35% w/w. This document also discloses a process for preparation of the said composition from plant sources namely Cinnamon, *Litchi* and *Arachis*. Further, this document teaches use of the said composition for treatment and management of HIV infection, AIDS and Influenza virus infection. However, this document does not suggest or teach the use of the said composition in treatment, prevention and management of broncho-constrictive conditions.

WO2007053641 A2 teaches that A-type procyanidins inhibit COX-2 gene transcription in a cell line. Based on this cell line experiment it extrapolates and speculates potential anti-inflammatory action in in-vivo conditions. However, this document does not motivate or demonstrate the action of A-type procyanidins in treating, preventing and managing broncho-constrictive conditions namely allergic rhinitis, asthma and COPD. Inhibition of COX-2 enzyme synthesis as discussed by this document has no implication on secretion of leukotrienes. Leukotrienes are the mediators involved in inflammation of the bronchiols or the airway in broncho-constrictive conditions namely allergic rhinitis, asthma and COPD. Moreover, inhibition of COX-2 enzyme can have adverse effect in broncho-constrictive conditions since it inhibits secretion of prostaglandin E2 (PGE2). According to Simmons et al. (2004), PGE2 has bronchoprotective effect in asthma and other pulmonary conditions. For example, aspirin-induced asthma may be triggered by increased release of leukotrienes from inflammatory cells caused by removal of the inhibitory influence of PGE2, a major product of COX-2 in airways. Beside, recent scientific research showed that inhibition of COX-2 has pronounced adverse cardiovascular side effects which lead to withdrawal best selling approved COX-2 inhibitor drugs like Vioxx from the market. Hence, WO2007053641 A2 does not motivate or teach a person skilled in the art to investigate A-type procyanidins for treating, preventing and managing broncho-constrictive conditions namely allergic rhinitis, asthma and COPD.

STATEMENT OF DISCLOSURE

Accordingly, the present disclosure relates to a method of managing broncho-constrictive condition, said method comprising act of administering a composition comprising pentameric type A procyanidin, trimeric procyanidin and tetrameric procyanidin, optionally along with one or more pharmaceutical excipient, to subject in need thereof.

DETAILED DESCRIPTION

The present disclosure relates to a method of managing broncho-constrictive condition, said method comprising act of administering a composition comprising pentameric type A procyanidin, trimeric procyanidin and tetrameric procyanidin, optionally along with one or more pharmaceutical excipient, to subject in need thereof.

In an embodiment of the present disclosure, the broncho-constrictive condition is selected from group comprising allergic rhinitis, asthma and chronic obstructive pulmonary disease or any combinations thereof.

In another embodiment of the present disclosure, the pentameric type A procyanidin is at concentration ranging from about 55% w/w to about 99% w/w, the trimeric procyanidin and the tetrameric procyanidin are each at concentration ranging from about 0.5% w/w to about 35% w/w; and the pharmaceutical excipient is at concentration ranging from about 0.5% to about 99.9%.

In yet another embodiment of the present disclosure, the pentameric type A procyanidin is at concentration ranging from about 80% w/w to about 90% w/w, the trimeric procyanidin and the tetrameric procyanidin are each at concentration ranging from about 0.5% w/w to about 20% w/w.

In still another embodiment of the present disclosure, the pharmaceutical excipient is selected from group comprising gums, granulating agents, binders, lubricants, disintegrating agents, sweetening agents, additives, solvents, glidants, anti-adherents, anti-static agents, surfactants, anti-oxidants, surfactants, viscocity enhancers, plant cellulosic material coloring agents, flavoring agents, coating agents, plasticizers, preservatives, suspending agents, emulsifying agents, anti-static agents and spheronization agents or any combinations thereof.

In still another embodiment of the present disclosure, the composition is formulated into dosage forms selected from group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, nasal spray, inhalers, nebulizers, intravenous injection, intravenous solutions, intramuscular injections, intramuscular depot, subcutaneous injection, percutaneous injection, phytoceuticals, nutraceuticals and food stuffs or any combinations thereof.

In still another embodiment of the present disclosure, the composition is administered at dose ranging from about 1 mg/kg to about 100 mg/kg body weight of the subject.

In still another embodiment of the present disclosure, the composition is administered as a spray at dose ranging from about 1 µg/kg to about 25 µg/kg body weight of the subject.

In still another embodiment of the present disclosure, the subject is a mammal, including but not limiting to human beings.

In an embodiment of the present disclosure, the term managing or management includes preventing and treating of a disease condition or disorder or ill effects or side effects. The term also encompasses maintenance of the optimum state and prevention of the further progress in the disease condition or disorder or ill effects or side effects.

The present disclosure relates to a method of managing broncho-constrictive conditions in a subject in need thereof, wherein said method comprises step of administering pharmaceutically effective amount of a composition comprising pentameric type-A procyanidin, trimers and tetramers of procyanidin, optionally along with pharmaceutically acceptable excipient(s).

In yet another embodiment of the present disclosure, the concentration of pentameric procyanidin flavonoid is ranging from about 80% w/w to about 99% w/w, trimers and tetramers of procyanidin flavonoid each at concentration ranging from about 0.5% w/w to about 20% w/w.

In still another embodiment of the present disclosure, said excipient is selected from a group comprising gums, granulating agents, binders, lubricants, disintegrating agents, sweetening agents, additives, solvents, glidants, anti-adherents, anti-static agents, surfactants, anti-oxidants, surfactants, viscocity enhancers, plant cellulosic material coloring agents, flavoring agents, coating agents, plasticizers, preservatives, suspending agents, emulsifying agents, antistatic agents, and spheronization agents or any combination thereof.

In still another embodiment of the present disclosure, said composition is formulated into various dosage forms selected from a group comprising tablet, troches, lozenges, aqueous or oily suspensions, liquid, ointment, patch, gel, lotion, dentifrice, capsule, emulsion, creams, spray, drops, dispersible powders or granules, emulsion in hard or soft gel capsules, syrups, elixirs, nasal spray, inhalers, nebulizers, intravenous injection, Intravenous solutions, Intramuscular injections, Intramuscular depot, subcutaneous injection, percutaneous injection, phytoceuticals, nutraceuticals and food stuffs or any combination thereof.

In an embodiment of the present disclosure the composition is used for the prevention, treatment and management of broncho-constrictive conditions like Allergic Rhinitis, Asthma, and Chronic obstructive pulmonary disease (COPD).

In another embodiment of the present disclosure, the activity can be treatment, management or preventive in nature.

In another embodiment of the present disclosure, the monomeric unit of the composition is chosen from a group of catechins, preferable catechin or epicatechin.

In still another embodiment of the present disclosure, this composition is administered to animals and human beings.

The disclosure is further elaborated with the help of following examples. However, these examples should not be construed to limit the scope of the disclosure.

EXAMPLES

Example 1

Pharmacokinetic Studies of Instant Composition

The Pharmacokinetic parameters of the instant composition is studied in healthy rats to determine the bioavailability of the instant composition. Male Swiss Wistar rats weighing about 150-200 gm are orally administered a single dose of present composition at about 100 mg/kg of body weight. Blood is withdrawn by retro orbital puncture at 0, 5, 15, 30, 60, 90, 120, 150, 180 minutes. Plasma is obtained by centrifugation of blood at about 10000 rpm at about 4° C. for about 20 min. Reverse Phase HPLC method described below has been developed for detection of the instant composition in the plasma.

Column: 150×4.6 mm C-18 Reverse Phase 5µ
Injection volume: about 20 µl
UV Detection Wavelength: about 280 nm
Mobile phase: 65 of 0.1% Aqueous Formic Acid & 35 of Acetonitrile Isocratic
Flow rate: 1 ml/min The present composition showed a plasma half life ($T_{1/2}$) of about 4 hrs and maximum plasma concentration ($C_{max}$) of about 109.213 µg/ml.

Example 2

In-Vivo Pulmonary Antigen-Induced Sensitization Study of Instant Composition

Prophylactic activity of instant composition against antigen-induced broncho-constriction is tested in sensitized guinea pigs. Male Duncan Hartley derived guinea pigs (400±50 g) are pretreated with instant composition at dose of about 100 mg/kg of body weight of the subject, administered orally. One hour after pretreatment, the guinea pigs are sensitized with intraperitoneal injection of ovalbumin (0.5 µg). A cocktail of Indomethacin (about 10 mg/kg), Mepyramine (about 2 mg/kg) and Propanolol (about 100 mg/kg) is injected about 10 mins before sensitization in order to block other mediators of broncho-blockade. Sensitized animals are anesthetized and artificially ventilated.

In vehicle-treated animals, antigen challenge resulted in an increase in intratracheal pressure (ITP) ranging from about 45% to about 85% of maximum possible bronchoconstriction provoked by complete tracheal occlusion. Animals pretreated with instant composition showed significant inhibition of ovalbumin-induced broncho-constriction.

TABLE 1

Change in Intratracheal Pressure (ITP) in Response to Treatment

| Treatment Group | ΔITP (cm H$_2$O) | |
| --- | --- | --- |
| | Before Ovalbumin | After Ovalbumin |
| Vehicle Control | 0 | 29.3 ± 2.2 |
| instant composition (about 100 mg/kg) | 0 | 23.0 ± 2.0* |
| Phenidone (about 30 mg/kg) | 0 | 2.3 ± 0.3*** | n = 5;
Data Analyzed using One-way ANOVA followed by Dunnett's Multiple Comparison test;
*P < 0.05 and
**P < 0.001 as compared to Vehicle Control group.

No changes are observed in blood pressure and heart rate after 1 hour of administration of instant composition. Treatment with standard drug Phenidone reduced blood pressure 5 minutes after administration.

TABLE 2

Effect of Treatment on Heart Rate and Blood Pressure

| Treatment Group | Heart Rate (beats/minute) | Blood Pressure (mm Hg) |
| --- | --- | --- |
| Vehicle Control (measured 1 hour after administration) | 171.2 ± 3.4 | 49.4 ± 4.0 |
| instant composition (measured 1 hour after administration) | 184.4 ± 11.9 | 45.6 ± 3.0 |
| Phenidone (measured 5 mins after administration) | 162.4 ± 4.7 | 34.4 ± 1.9* | n = 5;
Data Analyzed using One-way ANOVA followed by Dunnett's Multiple Comparison test;
*P < 0.05 as compared to Vehicle Control group.

Results of the Pulmonary Antigen-induced Sensitization study as shown in Table Nos. 1 and 2, depicts direct benefit of instant composition in treating broncho-constrictive conditions without inducing any side-effects. Hence the instant composition is effective in treatment of broncho-constrictive conditions like Allergic Rhinitis, Asthma and Chronic obstructive pulmonary disease (COPD).

Example 3

Formulation of Instant Composition

The instant composition comprising type A pentameric procyanidin flavonoid of concentration ranging from about 55% w/w to about 99% w/w, trimers and tetramers of procyanidin flavonoid each at concentration ranging from about 0.5 w/w to about 35% w/w is formulated into capsules by blending with about 2% w/w of micro crystalline cellulose, about 0.5% w/w of crospovidone and about 0.2% w/w of magnesium stearate. This mixture is filled in capsules.

Example 4

Nasal Spray Formulation of Instant Composition

About 1.025 g of instant composition comprising type A pentameric procyanidin flavonoid of concentration ranging from about 55% w/w to about 99% w/w, trimers and tetramers of procyanidin flavonoid each at concentration ranging from about 0.5% w/w to about 35% w/w is mixed with about 961.53 ml of normal saline, about 0.0871 mg menthol and about 38.46 ml of ethyl alcohol, agitated to get a clear solution. This mixture is sterilized, filtered through about 0.04 micron filter and filled in nasal spray bottles. One shot of the nasal spray delivers about 100 μl of the formulation which is equivalent to about 100 μg of instant composition.

Similar formulation of the instant composition is prepared by addition of appropriate excipient(s) selected from group comprising the following: granulating agents, binding agents, lubricating agents, disintegrating agents, sweetening agents, glidants, anti-adherents, anti-static agents, surfactants, antioxidants, gums, coating agents, coloring agents, flavouring agents, coating agents, plasticizers, preservatives, suspending agents, emulsifying agents, additives, solvents, surfactants, viscosity enhancers, antistatic agents, plant cellulosic material and spheronization agents or any combination thereof. And the type of formulation is selected from group comprising of tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, nasal spray, inhalers, nebulizers, intravenous injection, intravenous solutions, intramuscular injections, intramuscular depot, subcutaneous injection, percutaneous injection, phytoceuticals, nutraceuticals and food stuffs or any combination thereof. Depending on the route of administration, different excipients/carriers are used. Those skilled in art will know to choose a suitable formulation of the instant composition for treatment, prevention and management of broncho-constrictive conditions.

Example 5

Anecdotal Study in Allergic Rhinitis Patients

A study to assess the efficacy of the instant composition against 2 patients with perennial allergic rhinitis (PAR) and 1 patient with seasonal allergic rhinitis (SAR) is conducted. Patient 1 with PAR is administered about two to three shots twice daily, each shot comprising 100 μg of instant composition in nasal spray formulation. This is equivalent to 5 to 20 μg/kg of body weight of the subject, of instant composition. Patient 2 with PAR and Patient 3 with SAR received about 350 mg capsules of instant composition twice daily, equivalent to about 10 to 25 mg/kg of body weight of the subject per day. The treatment is carried out for a period of 2 months. The efficacy of the instant composition is analyzed on the basis of patient reported outcome taken at the beginning and end of the study period.

TABLE 3

EFFECT ON TREATMENT OF ALLERGIC RHINITIS

| Mini Rhinoconjuntivitis Quality of Life Questionnaire | Patient Reported Outcome† | | | | | |
|---|---|---|---|---|---|---|
| | Patient 1 | | Patient 2 | | Patient 3 | |
| | Before | After | Before | After | Before | After |
| Regular Activities at Home and at Work | 5 | 0 | 6 | 0 | 6 | 0 |
| Recreational Activities | 6 | 0 | 6 | 0 | 6 | 0 |
| Sleep | 4 | 0 | 5 | 0 | 6 | 0 |
| Need to Rub Nose/Eyes | 5 | 0 | 5 | 1 | 6 | 1 |
| Need to Blow Nose Repeatedly | 6 | 0 | 6 | 0 | 6 | 0 |
| Sneezing | 5 | 0 | 6 | 0 | 6 | 0 |
| Stuffy/Blocked Nose | 5 | 1 | 5 | 1 | 6 | 0 |
| Runny Nose | 5 | 0 | 6 | 0 | 6 | 0 |
| Itchy Nose | 5 | 0 | 4 | 0 | 6 | 0 |
| Sore Eyes | 4 | 0 | 5 | 0 | 6 | 0 |
| Watery Eyes | 4 | 0 | 5 | 0 | 6 | 0 |
| Tiredness and/or Fatigue | 5 | 0 | 6 | 0 | 6 | 0 |
| Thirst | 4 | 0 | 6 | 0 | 6 | 0 |
| Feeling Irritable | 5 | 0 | 6 | 0 | 6 | 0 |

†Scale of Severity of symptoms (0—Not troubled; 1—Hardly troubled at all; 2—Somewhat troubled; 3—Moderately troubled; 4—Quite a bit troubled; 5—Very troubled; 6—Extremely troubled).

All patients administered with the instant composition reported significant reduction in symptoms of allergic rhinitis and immediate effect. Patients also reported improvement in overall quality of living as seen from the patient reported outcome of mini Rhinoconjuntivitis Quality of Life Questionnaire in Table 3. Hence the instant composition is useful in treating and managing both seasonal and perennial allergic rhinitis.

Example 6

Anecdotal Study in Asthma Patients

A study to assess the efficacy of the instant composition against 2 patients with chronic asthma is conducted. The subjects are given capsules of the instant composition at dose of about 350 mg twice daily for a period of 3 months, equivalent to about 10 to 25 mg/kg of body weight of the subject per day. The efficacy of the instant composition is analyzed on the basis of patient reported outcome taken at the beginning and end of the study period.

TABLE 4

EFFECT ON TREATMENT OF ASTHMA

| Asthma Questionnaire | Patient Reported Outcome† | | | |
|---|---|---|---|---|
| | Patient 1 | | Patient 2 | |
| | Before | After | Before | After |
| Coughing, Wheezing, Chest Tightness or Shortness of Breath during regular activities/exercise | 5 | 1 | 5 | 2 |
| Coughing, Wheezing, Chest Tightness or Shortness of Breath during sleep | 4 | 0 | 5 | 1 |
| Frequency of Asthma Attack | 5 | 0 | 5 | 1 |
| Faint or feeling dizzy | 4 | 0 | 5 | 0 |
| Need for SOS inhaler | 5 | 1 | 5 | 2 |

†Scale of Severity of symptoms (0—Absence; 1—Hardly Noticed; 2—Mild; 3—Moderate; 4—Strong; 5—Very Strong).

Both patients reported reduction in the number of asthma attacks following treatment with the instant composition. Significant reduction in asthmatic symptoms is reported while carrying out day to day activities, exercise and sleep. One of the patients also reported reduced need for reliever inhaler. Hence the instant composition is useful in treating, preventing and managing asthma.

The present invention demonstrates use of a pharmaceutically effective amount of a composition comprising type-A pentameric procyanidin flavonoid of concentration ranging from about 55 w/w to about 99% w/w, trimers and tetramers of procyanidin flavonoid each at a concentration ranging from about 0.5% w/w to about 35% w/w, optionally along with pharmaceutically acceptable excipient(s), for managing broncho-constrictive condition(s).

We claim:

1. A method of treating broncho-constrictive condition, said method comprising act of administering a composition consisting of pentameric type A procyanidin, trimeric type A procyanidin and tetrameric type A procyanidin optionally along with one or more pharmaceutical excipient, to subject in need thereof.

2. The method as claimed in claim 1, wherein the broncho-constrictive condition is selected from group comprising allergic rhinitis, asthma and chronic obstructive pulmonary disease or any combinations thereof.

3. The method as claimed in claim 1, wherein the pentameric type A procyanidin is at concentration ranging from about 55% w/w to about 99% w/w, the trimeric type A procyanidin and the tetrameric type A procyanidin are each at concentration ranging from about 0.5% w/w to about 35% w/w; and the pharmaceutical excipient is at concentration ranging from about 0.5% to about 99.9%.

4. The method as claimed in claim 3, wherein the pentameric type A procyanidin is at concentration ranging from about 80% w/w to about 90% w/w, the trimeric type A procyanidin and the tetrameric type A procyanidin are each at concentration ranging from about 0.5% w/w to about 20% w/w.

5. The method as claimed in claim 1, wherein the pharmaceutical excipient is selected from group comprising gums, granulating agents, binders, lubricants, disintegrating agents, sweetening agents, additives, solvents, glidants, anti-adherents, anti-static agents, surfactants, anti-oxidants, surfactants, viscocity enhancers, plant cellulosic material coloring agents, flavoring agents, coating agents, plasticizers, preservatives, suspending agents, emulsifying agents, antistatic agents and spheronization agents or any combinations thereof.

6. The method as claimed in claim 1, wherein the composition is formulated into dosage forms selected from group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, nasal spray, inhalers, nebulizers, intravenous injection, intravenous solutions, intramuscular injections, intramuscular depot, subcutaneous injection, percutaneous injection, phytoceuticals, nutraceuticals and food stuffs or any combinations thereof.

7. The method as claimed in claim 1, wherein the composition is administered at dose ranging from about 1 mg/kg to about 100 mg/kg body weight of the subject.

8. The method as claimed in claim 1, wherein the composition is administered as a spray at dose ranging from about 1 μg/kg to about 25 μg/kg body weight of the subject.

9. The method as claimed in claim 1, wherein the subject is a mammal.

10. The method of claim 2, wherein the allergic rhinitis is selected from group comprising seasonal allergic rhinitis, perennial allergic rhinitis and pollen allergic rhinitis or any combination thereof.

11. The method of claim 2 or 10, wherein symptoms of the allergic rhinitis is selected from group comprising rhinorrhoea, nasal congestion, obstruction, and pruritus triggered by contact with allergens selected from group comprising bacteria, viruses, animal parasites, dust, pollen, chemicals, food, drugs and smoke or any combination thereof.

\* \* \* \* \*